(12) United States Patent
Bleeker et al.

(10) Patent No.: US 12,183,454 B2
(45) Date of Patent: Dec. 31, 2024

(54) ARTIFICIAL INTELLIGENCE BASED TECHNOLOGIES FOR IMPROVING PATIENT INTAKE

(71) Applicant: CDW LLC, Vernon Hills, IL (US)

(72) Inventors: Casey Bleeker, Denver, CO (US); Nathan A. Cartwright, Cincinnati, OH (US)

(73) Assignee: CDW LLC, Vernon Hills, IL (US)

(*) Notice: Subject to any disclaimer, the term of this patent is extended or adjusted under 35 U.S.C. 154(b) by 207 days.

(21) Appl. No.: 17/940,603

(22) Filed: Sep. 8, 2022

(65) Prior Publication Data
US 2023/0082014 A1 Mar. 16, 2023

Related U.S. Application Data

(60) Provisional application No. 63/242,893, filed on Sep. 10, 2021.

(51) Int. Cl.
| | |
|---|---|
| *G16H 40/20* | (2018.01) |
| *G06F 40/40* | (2020.01) |
| *G16H 20/00* | (2018.01) |
| *G16H 70/20* | (2018.01) |

(52) U.S. Cl.
CPC ............ *G16H 40/20* (2018.01); *G06F 40/40* (2020.01); *G16H 20/00* (2018.01); *G16H 70/20* (2018.01)

(58) Field of Classification Search
CPC ..... G16H 40/20; G06F 16/2455; G06F 40/30; G06Q 10/1095; G10L 15/063; G10L 15/1815; G10L 15/22; G10L 15/30; G10L 2015/223; H04M 1/656; H04M 2201/40
See application file for complete search history.

(56) References Cited

U.S. PATENT DOCUMENTS

| | | | |
|---|---|---|---|
| 8,364,501 B2 * | 1/2013 | Rana | G16H 40/20 |
| | | | 705/2 |
| 9,536,049 B2 * | 1/2017 | Brown | G10L 15/08 |
| 9,824,188 B2 * | 11/2017 | Brown | G06F 3/04886 |
| (Continued) | | | |

OTHER PUBLICATIONS

International Application No. PCT/US2022/042974, International Search Report and Written Opinion, mailed Dec. 5, 2022.

*Primary Examiner* — Michael I Ezewoko
(74) *Attorney, Agent, or Firm* — MARSHALL, GERSTEIN & BORUN LLP; Randall G. Rueth

(57) ABSTRACT

Artificial intelligence (AI) based technologies for improving patient intake are disclosed herein. An example method includes receiving a patient intake request from a user; initiating, based on the patient intake request, a patient intake data stream including verbal responses from the user regarding patient intake of the user; applying, while simultaneously receiving the patient intake data stream, a natural language processing (NLP) model to the verbal responses from the user to output (i) textual transcriptions and (ii) intent interpretations; generating, by a care plan generation module, a recommended care plan based on the textual transcriptions and the intent interpretations; identifying, by an intent interpretation fulfillment module, one or more recipient entities to receive the textual transcriptions and the recommended care plan; and transferring the textual transcriptions and the recommended care plan to one or more recipient entity devices of the one or more recipient entities.

17 Claims, 3 Drawing Sheets

(56) References Cited

U.S. PATENT DOCUMENTS

| | | | |
|---|---|---|---|
| 10,181,252 B2* | 1/2019 | Pauws | H04L 67/306 |
| 10,796,560 B2* | 10/2020 | Pauws | G08B 25/016 |
| 10,827,071 B1* | 11/2020 | Adibi | H04L 67/53 |
| 11,024,142 B2* | 6/2021 | Tunnell | G08B 21/0415 |
| 11,029,918 B2* | 6/2021 | Brown | G10L 15/08 |
| 11,056,245 B2* | 7/2021 | Costantino | G16H 10/60 |
| 11,158,179 B2* | 10/2021 | Tunnell | G08B 27/001 |
| 11,606,463 B1* | 3/2023 | Yeracaris | H04M 3/5232 |
| 11,688,509 B2* | 6/2023 | Hanson | G10L 25/63 |
| | | | 705/2 |
| 11,775,780 B2* | 10/2023 | Joao | H04W 4/80 |
| | | | 340/10.1 |
| 11,849,379 B1* | 12/2023 | Vanetik | G16H 50/80 |
| 2010/0185465 A1* | 7/2010 | Rana | G16H 10/20 |
| | | | 705/2 |
| 2014/0074454 A1* | 3/2014 | Brown | G10L 15/08 |
| | | | 704/235 |
| 2014/0337048 A1* | 11/2014 | Brown | G06F 3/04886 |
| | | | 705/2 |
| 2017/0329922 A1* | 11/2017 | Eberting | G16H 40/67 |
| 2018/0039737 A1* | 2/2018 | Dempers | G06F 21/35 |
| 2018/0068082 A1* | 3/2018 | Brown | G10L 15/08 |
| 2018/0113987 A1* | 4/2018 | Zhu | G16H 40/63 |
| 2019/0051144 A1* | 2/2019 | David | G08B 21/0415 |
| 2019/0088101 A1* | 3/2019 | Tunnell | G08B 21/02 |
| 2019/0088373 A1* | 3/2019 | Sarmentero | G16H 40/67 |
| 2019/0122532 A1* | 4/2019 | Pauws | H04L 67/306 |
| 2019/0197861 A1* | 6/2019 | Tunnell | A61B 5/0205 |
| 2019/0355450 A1* | 11/2019 | Altstadter | G16H 40/20 |
| 2020/0227161 A1* | 7/2020 | Hanson | G06N 3/08 |
| 2020/0244605 A1* | 7/2020 | Nagaraja | H04L 51/02 |
| 2020/0258054 A1* | 8/2020 | Kaufman | G06Q 10/1095 |
| 2021/0004824 A1* | 1/2021 | Adibi | G06N 5/02 |
| 2021/0327582 A1* | 10/2021 | Joshi | G16H 50/20 |
| 2022/0101710 A1* | 3/2022 | Tunnell | A61B 5/746 |
| 2022/0277154 A1* | 9/2022 | Joao | H04W 4/12 |
| 2023/0069370 A1* | 3/2023 | Rao | G06Q 10/1095 |
| 2023/0385571 A1* | 11/2023 | Joao | H04W 4/12 |

* cited by examiner

ARTIFICIAL INTELLIGENCE BASED TECHNOLOGIES FOR IMPROVING PATIENT INTAKE

CROSS-REFERENCE TO RELATED APPLICATIONS

This application claims the benefit of U.S. Provisional Application No. 63/242,893, filed Sep. 10, 2021, and entitled "Artificial Intelligence Based Technologies for Improving Patient Intake", which is incorporated herein by reference in its entirety.

FIELD OF THE DISCLOSURE

The present disclosure is generally directed to technologies for patient intake and, more particularly, to artificial intelligence (AI) techniques for improving patient intake.

BACKGROUND

Generally, patient intake is a time-consuming process that can occupy valuable medical resources by preventing and/or otherwise reducing the ability of nurses and other trained medical professionals to perform medical procedures. Some medical providers rely on contact centers to alleviate this issue by automatically performing patient intake without the need of a medical staff member. However, these conventional contact centers suffer from several problems.

Conventional contact centers typically rely on legacy communication protocols that inefficiently and erroneously obtain patient intake information. Thus, conventional contact centers often misdirect/transfer patients to destinations where the patient is either unable to continue the intake process, or fail to provide any obtained intake data to the entity receiving the patient, thereby further prolonging the intake process and delaying appropriate medical care. Namely, conventional contact centers bifurcate intake duties by transferring data to a remote platform for processing (e.g., transcription, interpretation). As a result, conventional contact centers frequently transfer patients to another intake service (e.g., human operator) without also transmitting the processed intake data.

Correspondingly, a major point of emphasis in the healthcare industry is accurately and efficiently performing patient intake, as this can pose a substantial challenge for traditional systems. Accordingly, there is a need for artificial intelligence (AI) based technologies for improving patient intake by quickly and seamlessly generating patient intake data to facilitate consistent and reliable patient intake, and by extension, medical care.

BRIEF DESCRIPTION OF THE DRAWINGS

The figures described below depict various aspects of the system and methods disclosed therein. It should be understood that each figure depicts one embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

The figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION

The embodiments described herein relate to, inter alia, artificial intelligence (AI) based technologies for improving patient intake. Specifically, the present techniques enable efficient and accurate patient intake by applying a trained natural language processing (NLP) model to verbal responses of a user, generating a recommended care plan with a care plan generation module based on the transcriptions and interpretations of the verbal responses, and identifying a recipient entity to continue/complete/review the user's patient intake using an intent interpretation fulfillment module based on the textual transcriptions of the verbal responses. The present techniques differ from traditional patient intake at least in that they streamline the intake process, such that the human resources (e.g., medical staff manually performing/re-performing patient intakes), processing resources, memory resources, and time required to perform patient intake are greatly reduced.

Exemplary Computing Environment

Figure 1:
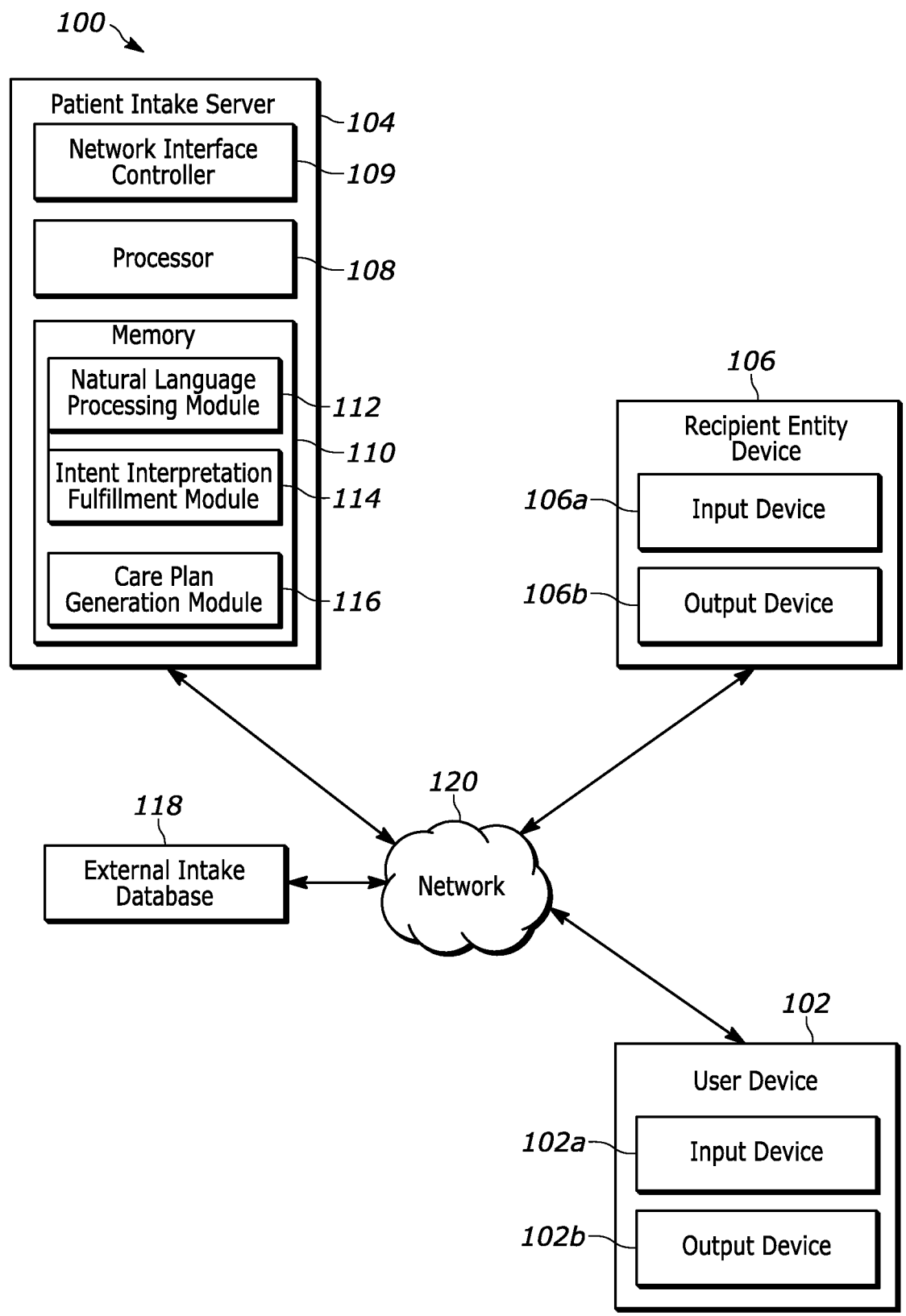
FIG. 1 depicts an exemplary computing environment in which artificial intelligence (AI) based technologies for improving patient intake may be implemented, in accordance with embodiments described herein.

FIG. 1 depicts an exemplary computing environment 100 in which the techniques disclosed herein may be implemented, according to an embodiment. The environment 100 includes a user device 102, a patient intake server 104, a recipient entity device 106, an external intake database 118, and a network 120. Some embodiments may include a plurality of user devices 102, a plurality of recipient entity devices 106, a plurality of patient intake servers 104, and/or a plurality of external intake databases 118.

Generally, the user device 102 may include an input device 102a and an output device 102b. The input device 102a may include any suitable device or devices for receiving input, such as one or more microphone, one or more camera, a hardware keyboard, a hardware mouse, a capacitive touch screen, etc. The output device 102b may include any suitable device for conveying output, such as a hardware speaker, a computer monitor, a touch screen, etc. In some cases, the input device 102a and the output device 102b may be integrated into a single device, such as a touch screen device that accepts user input and displays output.

The recipient entity device 106 may include an input device 106a and an output device 106b. The input device 106a may include any suitable device or devices for receiving input, such as one or more microphone, one or more camera, a hardware keyboard, a hardware mouse, a capacitive touch screen, etc. The output device 106b may include any suitable device for conveying output, such as a hardware speaker, a computer monitor, a touch screen, etc. In some cases, the input device 106a and the output device 106b may be integrated into a single device, such as a touch screen device that accepts user input and displays output. The recipient entity device 106 may be a healthcare provider device, and/or any other suitable provider that may interact with the user (e.g., via the user device 102) based on the patient intake performed by executable instructions stored on the patient intake server 104.

The patient intake server 104 may be an individual server, a group (e.g., cluster) of multiple servers, or another suitable type of computing device or system (e.g., a collection of computing resources). In some embodiments, one or more components of the patient intake server 104 may be embodied by one or more virtual instances (e.g., a cloud-based virtualization service). In such cases, one or more patient intake server 104 may be included in a remote data center (e.g., a cloud computing environment, a public cloud, a private cloud, etc.).

The patient intake server 104 includes a processor 108 and a network interface controller (NIC) 109. The processor 108 may include any suitable number of processors and/or processor types, such as CPUs and one or more graphics processing units (GPUs). Generally, the processor 108 is configured to execute software instructions stored in a memory 110. The memory 110 may include one or more persistent memories (e.g., a hard drive/solid state memory) and stores one or more set of computer executable instructions/modules, including an NLP module 112, and a intent interpretation fulfillment module 114.

The NIC 109 may include any suitable network interface controller(s), such as wired/wireless controllers (e.g., Ethernet controllers), and facilitate bidirectional/multiplexed networking over the network 120 between the patient intake server 104 and other components of the environment 100 (e.g., user device 102, the external intake database 118, the recipient entity device 106, etc.).

Each of the modules stored in memory 110 implement specific functionality. For example, in an embodiment, the intent interpretation fulfillment module 114 includes computer-executable instructions that, when executed, cause a computer to access one or more electronic databases (e.g., external intake database 118). For example, the intent interpretation fulfillment module 114 may include a library of application programming interfaces (APIs) configured to access and otherwise fulfill requests included within the intent interpretations of a user's verbal responses. For example, the intent interpretation fulfillment module 114 may access an electronic database via a socket, a persistent network connection, or any other suitable means. In some cases, an electronic database may reside entirely in the memory 114 (i.e., an in-memory database). The intent interpretation fulfillment module 114 may load one or more databases/tables into the in-memory database. Other modules in the memory 110 may use the intent interpretation fulfillment module 114 to access one or more electronic databases. For example, the care plan generation module 116 may access the intent interpretation fulfillment module 114 to retrieve data from the external intake database 118.

The care plan generation module 116 includes instructions for filtering textual transcriptions and intent interpretations to facilitate recommended care plan generation. Generally, the care plan generation module 116 retrieves data from medical diagnostic libraries and applies a set of rules to determine a recommended care plan for a particular user. The medical diagnostic libraries may be stored locally in memory 110, and/or as part of the external intake database 118. For example, the care plan generation module 116 may recover a set of medical diagnostic rules/principles from the external intake database 118 in response to receiving textual transcriptions and intent interpretations as part of a patient intake. The care plan generation module 116 may then apply the retrieved medical diagnostic rules to the textual transcriptions and intent interpretations to automatically generate a recommended care plan for the user.

The NLP module 112 includes computer-executable instructions for training and operating an NLP model. In general, the NLP module 112 may train one or more NLP models by establishing a network architecture, or topology, and adding layers that may be associated with one or more activation functions (e.g., a rectified linear unit, softmax, etc.), loss functions and/or optimization functions. One or more types of artificial neural networks may be employed, including without limitation, recurrent neural networks, convolutional neural networks, and/or deep learning neural networks. Data sets used to train the artificial neural network(s) may be divided into training, validation, and testing subsets, and these subsets may be encoded in an N-dimensional tensor, array, matrix, or other suitable data structures. Training may be performed by iteratively training the network using labeled training samples.

Training of the artificial neural network may produce byproduct weights, or parameters which may be initialized to random values. The weights may be modified as the network is iteratively trained, by using one of several gradient descent algorithms, to reduce loss and to cause the values output by the network to converge to expected, or "learned", values. In embodiments, a regression neural network may be selected which lacks an activation function, wherein input data may be normalized by mean centering, to determine loss and quantify the accuracy of outputs. Such normalization may use a mean squared error loss function and mean absolute error. The artificial neural network model may be validated and cross-validated using standard techniques such as hold-out, K-fold, etc. In embodiments, multiple artificial neural networks may be separately trained and operated, and/or separately trained and operated in conjunction. In embodiments, a Bayesian model may be used to train the NLP model.

In embodiments, the one or more NLP models may include an artificial neural network having an input layer, one or more hidden layers, and an output layer. Each of the layers in the artificial neural network may include an arbitrary number of neurons. The plurality of layers may chain neurons together linearly and may pass output from one neuron to the next, or may be networked together such that the neurons communicate input and output in a non-linear way. In general, it should be understood that many configurations and/or connections of artificial neural networks are possible. For example, the input layer may correspond to input parameters that are given as full sentences, or that are separated according to word or character (e.g., fixed width) limits. The input layer may correspond to a large number of input parameters (e.g., one million inputs), in some embodiments, and may be analyzed serially or in parallel. Further, various neurons and/or neuron connections within the artificial neural network may be initialized with any number of weights and/or other training parameters. Each of the neurons in the hidden layers may analyze one or more of the input parameters from the input layer, and/or one or more outputs from a previous one or more of the hidden layers, to generate a decision or other output. The output layer may include one or more outputs, each indicating a prediction. In some embodiments and/or scenarios, the output layer includes only a single output.

In any event, the NLP model trained by the NLP module 112 may be trained with a plurality of verbal responses regarding patient intake of a plurality of users. The NLP model is configured to output one or more textual transcriptions and one or more intent interpretations corresponding to the one or more textual transcriptions.

The external intake database 118 may provide multiplexed access to any suitable medical diagnostic databases, tables, and/or any other suitable resource. For example, the external intake database 118 may be implemented as a relational database management (RDBMS) such as MySQL, Oracle, etc. The external intake database 118 may be a set of comma-separated (CSV) values, Microsoft Excel spreadsheets, etc. The external intake database 118 may be implemented in one or more computing devices (e.g., using one or more devices such as the patient intake server 104). The external intake database 118 may be implemented using one or more suitable cloud computing service (e.g., using a virtual server, or a hosted virtual database instance). The server(s) implementing the external intake database 118 may include one or more processor, a NIC, a memory, etc.

The network 120 may be a single communication network, or may include multiple communication networks of one or more types (e.g., one or more wired and/or wireless local area networks (LANs), and/or one or more wired and/or wireless wide area networks (WANs) such as the Internet). The network 120 may enable bidirectional communication between the user device 102, the patient intake server 104, the external intake database 118, and the recipient entity device 106, or between multiple recipient entity devices 106, for example.

Exemplary Workflow

Figure 2:
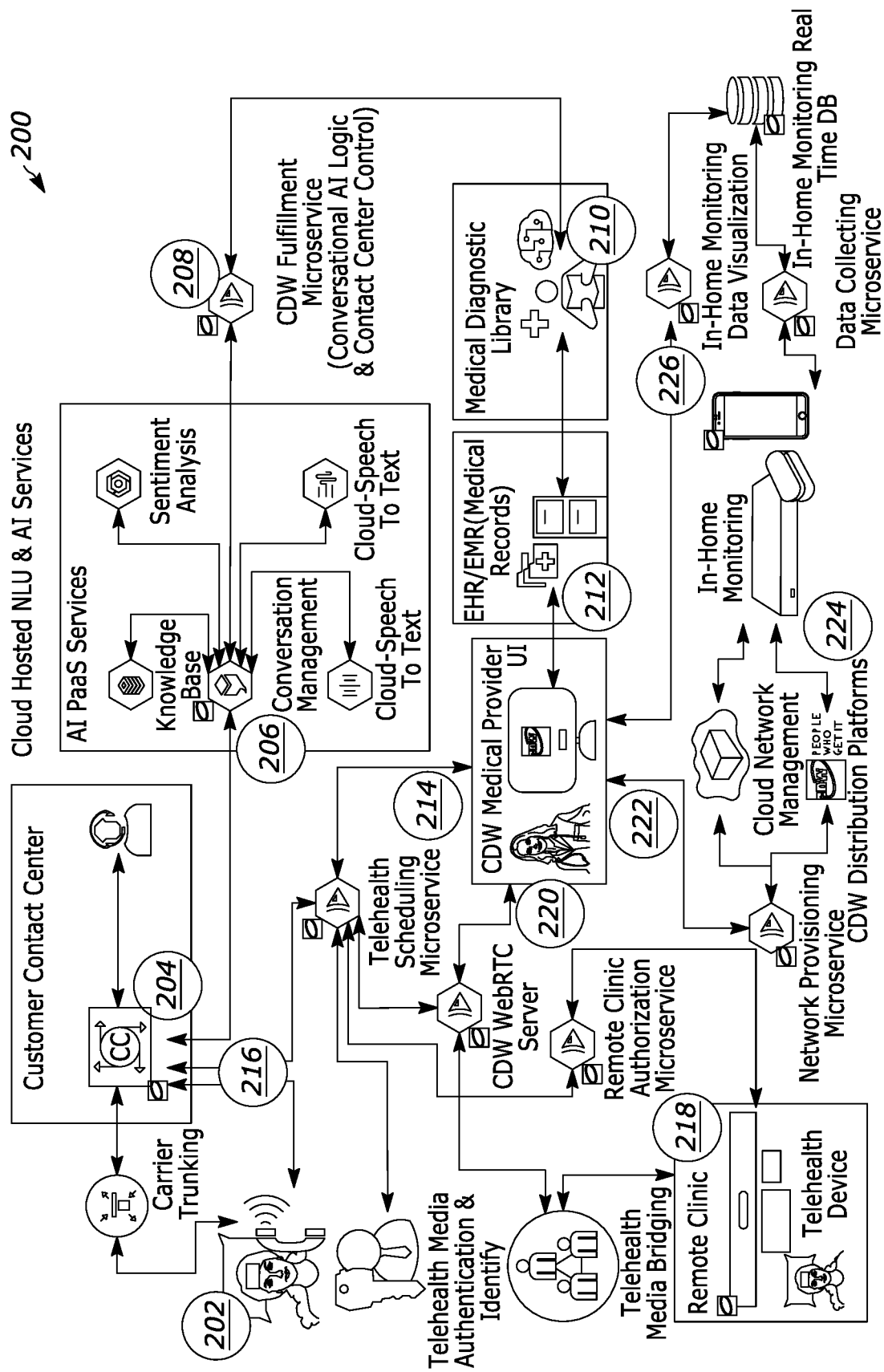
FIG. 2 depicts an exemplary workflow in which artificial intelligence (AI) based technologies for improving patient intake may be implemented, in accordance with embodiments described herein.

FIG. 2 depicts an exemplary workflow 200 in which artificial intelligence (AI) based technologies for improving patient intake may be implemented, in accordance with embodiments described herein.

As part of the exemplary computing environment 200, a patient (also referenced herein as a "user") may initiate a patient intake data stream 202. The contact center 204 receiving the call may include integrated AI (e.g., NLP module 112) in order to provide NLP capabilities, and the conversational AI 206 (e.g., including the NLP module 112) may generally communicate with the patient in order to complete the patient intake process.

The fulfillment microservice 208 (e.g., including the intent interpretation fulfillment module 114) may coordinate the conversation between the patient and the conversational AI 206 by utilizing medically approved questions from a medical diagnostic library 210 (e.g., external intake database 118). The NLP model may analyze the patient responses to the questions, and transmit that information to a care plan generation module in order to generate a recommended care plan.

The fulfillment microservice 208 may also coordinate transmission of the record of patient intake (e.g., textual transcriptions, intent interpretations, etc.) and/or the recommended care plan to a recipient entity 212 for medical analysis/review. The recipient entity 212 may review the records and prescribe a follow-up consult, which is transmitted to a telehealth scheduling microservice 214. As a result, the telehealth scheduling microservice 214 may initiate scheduling with the patient through an automated virtual assistant 216 that may contact the patient via any suitable means (e.g., SMS, phone call, etc.).

Thereafter, the patient may arrive at a remote clinic for a virtual consult, wherein a telehealth device 218 may authenticate the patient, and may automatically join the patient to a previously created user interface extensions, macros, and xAPI calls. These extensions, macros, and xAPI calls may be mediated by, for example, an authentication microservice. The medical provider may join the telehealth consult 220 natively through the provider's user interface (e.g., via the recipient entity device 106). The patient intake server 104, for example, may mediate guest tokens to facilitate access to the telehealth consult, and may verify the correct meeting information when the meeting initiates.

Following the consult, if the medical provider prescribes in-home monitoring, a network provisioning microservice 222 may leverage a cloud network management API to provision a cellular gateway, associated monitoring devices, and corresponding networking access. In an embodiment, drop shipment may be automated through the server. As a result, the patient may receive a pre-configured network and monitoring device(s) 224, and the medical monitoring devices may publish data to a collection microservice 226, that may render data visualization to the medical provider user interface in real-time.

Exemplary Method

Figure 3:
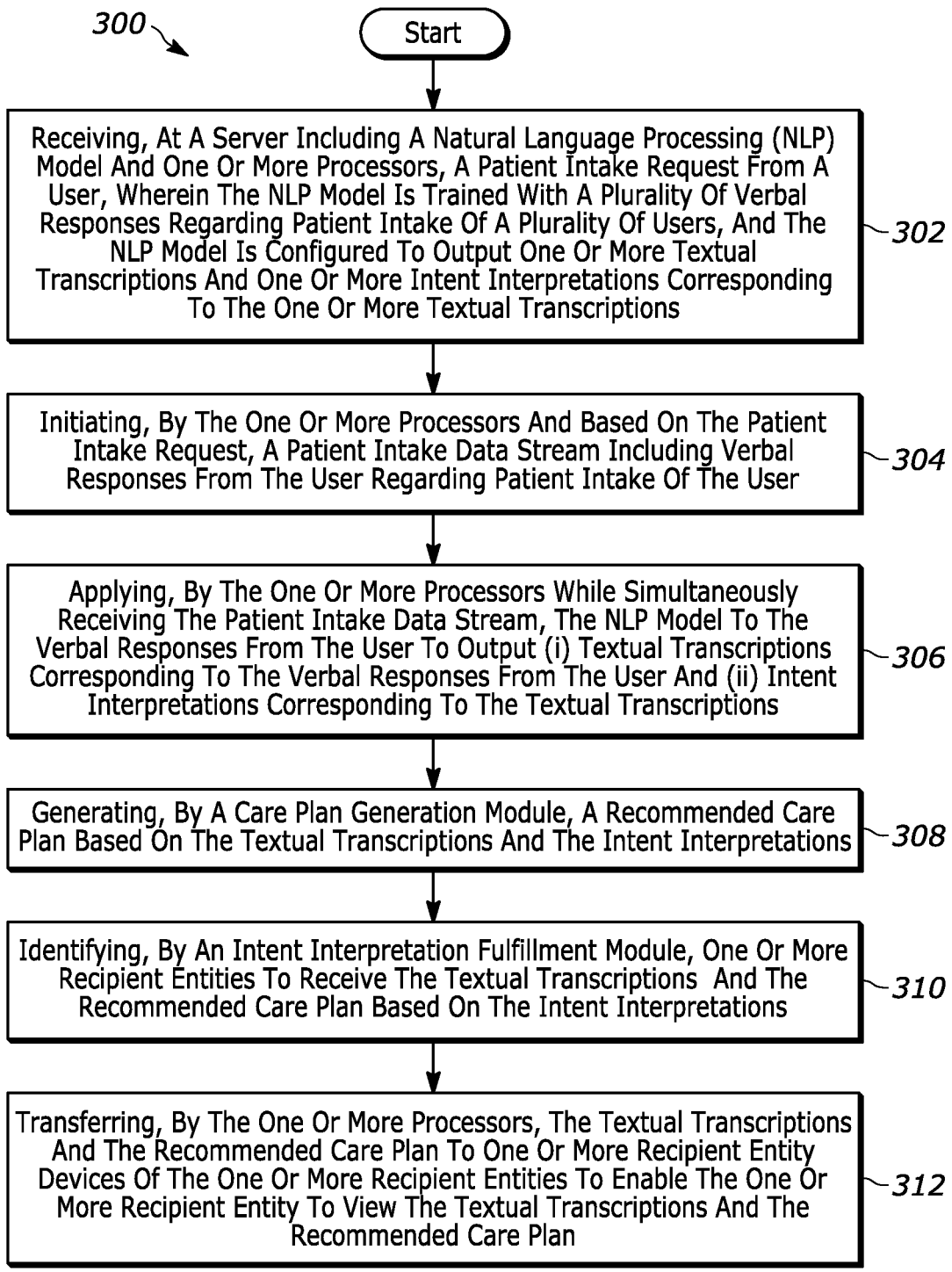
FIG. 3 is a flow diagram of an example AI based method for improving patient intake, in accordance with embodiments described herein.

FIG. 3 is a flow diagram of an example AI based method 300 for improving patient intake, in accordance with embodiments described herein. The example method 300 begins (block 302) when a server (e.g., patient intake server 104) receives a patient intake request from a user. The server may store a natural language processing (NLP) model, which may include natural language understanding (NLU) algorithms, natural language generation (NLG) algorithms, text-to-speech (TTS) algorithms, and/or any other suitable algorithms or combinations thereof. The NLP model may be trained with a plurality of verbal responses regarding patient intake of a plurality of users, and the NLP model is configured to output one or more textual transcriptions and one or more intent interpretations corresponding to the one or more textual transcriptions.

The example method 300 may continue when the one or more processors of the server initiate a patient intake data stream that includes verbal responses from the user regarding patient intake of the user (block 304). Generally, the patient intake data stream may include a phone call over a telephone network (e.g., network 120), but it should be understood that the patient intake data stream may include any suitable data stream, such as live video/audio data streaming, file sharing, etc.

The example method 300 may continue when the one or more processors of the server apply the NLP model to the verbal responses from the user to output (i) textual transcriptions corresponding to the verbal responses from the user and (ii) intent interpretations corresponding to the textual transcriptions (block 306).

The example method 300 may continue when a care plan generation module (e.g., care plan generation module 116) generates a recommended care plan based on the textual transcriptions and the intent interpretations (block 308).

The example method 300 may continue when an intent interpretation fulfillment module (e.g., intent interpretation fulfillment module 114), identifies one or more recipient entities to receive the textual transcriptions and the recommended care plan based on the intent interpretations (block 310). Additionally, the example method 300 may continue when the one or more processors of the server transfer the textual transcriptions and the recommended care plan to one or more recipient entity devices of the one or more recipient entities to enable the one or more recipient entity to view the textual transcriptions and the recommended care plan (block 312).

Additional Considerations

The following considerations also apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

It should also be understood that, unless a term is expressly defined in this patent using the sentence "As used herein, the term" "is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

Unless specifically stated otherwise, discussions herein using words such as "processing," "computing," "calculating," "determining," "presenting," "displaying, " or the like may refer to actions or processes of a machine (e.g., a computer) that manipulates or transforms data represented as physical (e.g., electronic, magnetic, or optical) quantities within one or more memories (e.g., volatile memory, nonvolatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" is employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for implementing the concepts disclosed herein, through the principles disclosed herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed:

1. An artificial intelligence (AI) based method for improving patient intake, the method comprising:
    receiving, at a server including a natural language processing (NLP) model and one or more processors, a patient intake request from a user, wherein the NLP model is trained based on a plurality of verbal responses regarding patient intake of a plurality of users, and the NLP model is configured to output one or more textual transcriptions and one or more intent interpretations corresponding to the one or more textual transcriptions, and wherein the NLP model is iteratively trained based on verbal responses;
    initiating, by the one or more processors and based on the patient intake request, a patient intake data stream including verbal responses from the user regarding patient intake of the user;
    applying, by the one or more processors while simultaneously receiving the patient intake data stream, the NLP model to the verbal responses from the user to output (i) textual transcriptions corresponding to the verbal responses from the user and (ii) intent interpretations corresponding to the textual transcriptions;
    generating, by a care plan generation module, a recommended care plan based on the textual transcriptions and the intent interpretations;
    identifying, by an intent interpretation fulfillment module, one or more recipient entities to receive the textual transcriptions and the recommended care plan based on the intent interpretations;
    transferring, by the one or more processors, the textual transcriptions and the recommended care plan to one or more recipient entity devices of the one or more recipient entities to enable the one or more recipient entity to view the textual transcriptions and the recommended care plan;
    receiving, at the one or more processors, an in-home monitoring request from a recipient entity;
    provisioning, by the one or more processors, a cellular gateway, a monitoring device, and networking access for the cellular gateway and the monitoring device;
    automatically scheduling, by the one or more processors, the cellular gateway and the monitoring device for shipment to the user;
    receiving, at the one or more processors, data from the monitoring device corresponding to the user; and
    causing, by the one or more processors, the data to render at a medical provider user interface in real-time.

2. The AI based method of claim 1, wherein initiating the patient intake data stream further comprises:
    receiving, at the server, a phone call from the user; and
    applying, by the one or more processors, the NLP model to the verbal responses in order to communicate with the user to complete the patient intake of the user.

3. The AI based method of claim 1, wherein generating the recommended care plan further comprises:
    retrieving, by the care plan generation module, a set of medical diagnostic rules from one or more medical diagnostic libraries; and applying, by the care plan generation module, the set of medical diagnostic rules to the textual transcriptions and the intent interpretations to automatically generate the recommended care plan.

4. The AI based method of claim 3, wherein the one or more medical diagnostic libraries are stored in a memory of the server.

5. The AI based method of claim 1, wherein transferring the textual transcriptions and the recommended care plan to the one or more recipient entity devices further comprises:
receiving, from a recipient entity device, a follow-up consult request; and
scheduling, by a telehealth scheduling microservice, the user for a follow-up consult with the recipient entity through an automated virtual assistant that contacts the user via at least one of: (i) a short message service (SMS) text message or (ii) a phone call.

6. The AI based method of claim 1, wherein transferring the textual transcriptions and the recommended care plan to the one or more recipient entity devices further comprises:
mediating, by the one or more processors, guest tokens that enable access to a follow-up consult between the user and a recipient entity; and
upon initiation of the follow-up consult, verifying, by the one or more processors, meeting information of the follow-up consult between the user and the recipient entity.

7. The AI based method of claim 1, wherein the one or more recipient entities includes a healthcare provider device to receive the textual transcriptions and the recommended care plan based on the intent interpretations.

8. An artificial intelligence (AI) based system for improving patient intake, the system comprising:
one or more processors; and
one or more memories communicatively coupled with the one or more processors, the one or more memories storing a care plan generation module, an intent interpretation fulfillment module, and a natural language processing (NLP) model that is trained based on a plurality of verbal responses regarding patient intake of a plurality of users, and the NLP model is configured to output one or more textual transcriptions and one or more intent interpretations corresponding to the one or more textual transcriptions, and wherein the NLP model is iteratively trained based on verbal responses, and
wherein the one or more memories store instructions thereon that, when executed by the one or more processors, cause the one or more processors to:
receive a patient intake request from a user,
initiate, based on the patient intake request, a patient intake data stream including verbal responses from the user regarding patient intake of the user,
apply, while simultaneously receiving the patient intake data stream, the NLP model to the verbal responses from the user to output (i) textual transcriptions corresponding to the verbal responses from the user and (ii) intent interpretations corresponding to the textual transcriptions,
generate, by the care plan generation module, a recommended care plan based on the textual transcriptions and the intent interpretations,
identify, by the intent interpretation fulfillment module, one or more recipient entities to receive the textual transcriptions and the recommended care plan based on the intent interpretations,
transfer the textual transcriptions and the recommended care plan to one or more recipient entity devices of the one or more recipient entities to enable the one or more recipient entity to view the textual transcriptions and the recommended care plan,
receive an in-home monitoring request from a recipient entity,
provisioning a cellular gateway, a monitoring device, and networking access for the cellular gateway and the monitoring device,
automatically scheduling the cellular gateway and the monitoring device for shipment to the user,
receiving data from the monitoring device corresponding to the user, and
causing the data to render at a medical provider user interface in real-time.

9. The AI based system of claim 8, wherein the instructions, when executed, further cause the one or more processors to initiate the patient intake data stream by:
receiving a phone call from the user; and
applying the NLP model to the verbal responses in order to communicate with the user to complete the patient intake of the user.

10. The AI based system of claim 8, wherein the instructions, when executed, further cause the one or more processors to generate the recommended care plan by:
retrieving, by the care plan generation module, a set of medical diagnostic rules from one or more medical diagnostic libraries; and
applying, by the care plan generation module, the set of medical diagnostic rules to the textual transcriptions and the intent interpretations to automatically generate the recommended care plan.

11. The AI based system of claim 10, wherein the one or more medical diagnostic libraries are stored in the one or more memories.

12. The AI based system of claim 8, wherein the one or more memories further store a telehealth scheduling microservice, and the instructions, when executed, further cause the one or more processors to transfer the textual transcriptions and the recommended care plan to the one or more recipient entity devices by:
receiving, from a recipient entity device, a follow-up consult request; and
scheduling, by the telehealth scheduling microservice, the user for a follow-up consult with the recipient entity through an automated virtual assistant that contacts the user via at least one of: (i) a short message service (SMS) text message or (ii) a phone call.

13. The AI based system of claim 8, wherein the instructions, when executed, further cause the one or more processors to transfer the textual transcriptions and the recommended care plan to the one or more recipient entity devices by:
mediating guest tokens that enable access to a follow-up consult between the user and a recipient entity; and
upon initiation of the follow-up consult, verifying meeting information of the follow-up consult between the user and the recipient entity.

14. The AI based system of claim 8, wherein the one or more recipient entities includes a healthcare provider device to receive the textual transcriptions and the recommended care plan based on the intent interpretations.

15. A tangible, non-transitory computer-readable medium storing instructions for improving patient intake, that when executed by one or more processors cause the one or more processors to:

receive a patient intake request from a user;
initiate, based on the patient intake request, a patient intake data stream including verbal responses from the user regarding patient intake of the user;
apply, while simultaneously receiving the patient intake data stream, a natural language processing (NLP) model to the verbal responses from the user to output (i) textual transcriptions corresponding to the verbal responses from the user and (ii) intent interpretations corresponding to the textual transcriptions, wherein the NLP model is trained based on a plurality of verbal responses regarding patient intake of a plurality of users, and the NLP model is configured to output one or more textual transcriptions and one or more intent interpretations corresponding to the one or more textual transcriptions, and wherein the NLP model is iteratively trained based on verbal responses;
generate a recommended care plan based on the textual transcriptions and the intent interpretations;
identify one or more recipient entities to receive the textual transcriptions and the recommended care plan based on the intent interpretations;
transfer the textual transcriptions and the recommended care plan to one or more recipient entity devices of the one or more recipient entities to enable the one or more recipient entity to view the textual transcriptions and the recommended care plan;
receive an in-home monitoring request from a recipient entity;
provision a cellular gateway, a monitoring device, and networking access for the cellular gateway and the monitoring device;
automatically schedule the cellular gateway and the monitoring device for shipment to the user;
receive data from the monitoring device corresponding to the user; and
cause the data to render at a medical provider user interface in real-time.

16. The tangible, non-transitory computer-readable medium of claim 15, wherein the instructions, when executed, further cause the one or more processors to generate the recommended care plan by:
retrieving a set of medical diagnostic rules from one or more medical diagnostic libraries; and
applying the set of medical diagnostic rules to the textual transcriptions and the intent interpretations to automatically generate the recommended care plan.

17. The tangible, non-transitory computer-readable medium of claim 15, wherein the instructions, when executed, further cause the one or more processors to transfer the textual transcriptions and the recommended care plan to the one or more recipient entity devices by:
mediating guest tokens that enable access to a follow-up consult between the user and a recipient entity; and
upon initiation of the follow-up consult, verifying meeting information of the follow-up consult between the user and the recipient entity.

* * * * *